US007638496B2

(12) United States Patent
Tam et al.

(10) Patent No.: US 7,638,496 B2
(45) Date of Patent: *Dec. 29, 2009

(54) NUCLEOSIDE ANALOGS WITH CARBOXAMIDINE MODIFIED MONOCYCLIC BASE

(75) Inventors: Robert Tam, Irvine, CA (US); Kandasamy Ramasamy, Aliso Viejo, CA (US); Zhi Hong, Aliso Viejo, CA (US); Johnson Lau, Newport Beach, CA (US)

(73) Assignee: Valeant Pharmaceuticals North America, Aliso Viejo, CA (US)

(*) Notice: Subject to any disclaimer, the term of this patent is extended or adjusted under 35 U.S.C. 154(b) by 855 days.

This patent is subject to a terminal disclaimer.

(21) Appl. No.: 10/227,235

(22) Filed: Aug. 22, 2002

(65) Prior Publication Data

US 2005/0159372 A1    Jul. 21, 2005

Related U.S. Application Data

(63) Continuation-in-part of application No. 09/595,365, filed on Oct. 5, 2000, now Pat. No. 6,455,508.

(60) Provisional application No. 60/182,676, filed on Feb. 15, 2000.

(51) Int. Cl.
*A01N 43/04* (2006.01)
*A61K 31/70* (2006.01)

(52) U.S. Cl. .............................. 514/43; 514/44; 514/45; 536/26.9; 536/27.2

(58) Field of Classification Search .................. 514/43, 514/44, 45; 536/26.9, 27.2
See application file for complete search history.

(56) References Cited

U.S. PATENT DOCUMENTS

| | | | |
|---|---|---|---|
| 3,798,209 A | 3/1974 | Witkowski et al. | |
| 3,962,211 A | 6/1976 | Townsend et al. | |
| 3,984,396 A | 10/1976 | Witkowski et al. | |
| 3,991,078 A | 11/1976 | Witkowski et al. | |
| 4,093,624 A | 6/1978 | Revankar et al. | |
| RE29,835 E | 11/1978 | Witkowski et al. | |
| 4,892,865 A | 1/1990 | Townsend et al. | |
| 4,950,652 A | 8/1990 | Carter | |
| 5,290,540 A | 3/1994 | Prince et al. | |
| 5,506,347 A | 4/1996 | Erion et al. | |
| 5,573,764 A | 11/1996 | Sykes et al. | |
| 5,665,721 A | 9/1997 | Bhagwat et al. | |
| 5,674,998 A | 10/1997 | Boyer et al. | |
| 5,767,097 A | 6/1998 | Tam | |
| 5,907,036 A | 5/1999 | Ramasamy et al. | |
| 6,063,628 A | 5/2000 | Loeb et al. | |
| 6,130,326 A | 10/2000 | Ramasamy et al. | |
| 6,277,836 B1 | 8/2001 | Borody | |
| 6,423,695 B1 * | 7/2002 | Tam et al. ................... 514/81 |
| 6,455,508 B1 * | 9/2002 | Ramasamy et al. ........... 514/43 |
| 6,495,677 B1 | 12/2002 | Ramasamy et al. | |
| 6,518,253 B1 | 2/2003 | Tam | |
| 6,552,183 B1 | 4/2003 | Ramasamy et al. | |
| 6,573,248 B2 | 6/2003 | Ramasamy et al. | |
| 6,610,665 B1 | 8/2003 | Bays et al. | |

FOREIGN PATENT DOCUMENTS

| | | |
|---|---|---|
| CA | 2198940 | 3/1996 |
| EP | 0286224 | 10/1988 |
| EP | 0308066 | 3/1989 |
| EP | 0312222 | 4/1989 |
| EP | 0341065 | 11/1989 |
| EP | 0343945 | 11/1989 |
| EP | 0346132 | 12/1989 |
| JP | 64-026593 | 1/1989 |
| NZ | 228390 | 12/1991 |
| NZ | 330784 | 2/1999 |
| RU | 94028670 | 4/1994 |
| WO | WO 89/05649 | 6/1989 |
| WO | WO 94/07479 | 4/1994 |
| WO | WO 94/22887 | 10/1994 |
| WO | WO 97/26883 | 7/1997 |
| WO | WO 98/16184 | 4/1998 |
| WO | WO 98/16186 | 4/1998 |
| WO | WO 98/39342 | 9/1998 |
| WO | WO 98/39344 | 9/1998 |
| WO | WO 99/45016 | 9/1999 |
| WO | WO 01/27114 | 4/2001 |

OTHER PUBLICATIONS

Gabrielsen, B. et al., "Synthesis and Antiviral Evaluation of N-carboxamidine-sbustituded Analogs . . . ," Journal of Med. Chem., p. 3231-3238, (Aug. 13, 1992).
Witkowski, J. et al., "Synthesis and Antiviral Activity of 1,2,4-Triazole-3-thiocarbxamide . . . ," Journal of Med. Chemistry, vol. 16 (No. 8), p. 935-937, (Aug. 13, 1973).
"Target Crohn's and Colitis," *Association of the British Pharmaceutical Industry*, Feb. 2002.
Definition of "prodrug" Mondofacto On-line Medical Dictionary (copyright 1997-2003- the Cancer Web Project).
FDA Clinical Trials on Inflammatory Bowel Disease (See, Study 2, dated Nov. 3, 1999).
Anderson et al. "Ribonucleosides structurally related to the antitumor antibiotic sangivamycin"J. Org. Chem. 42: 997-1000 (1977).

(Continued)

*Primary Examiner*—Patrick T Lewis
(74) *Attorney, Agent, or Firm*—McDermott Will & Emery LLP (57) ABSTRACT

Novel nucleoside analog compounds are disclosed. The novel compounds or pharmaceutically acceptable esters or salts thereof may be used in pharmaceutical compositions, and such compositions may be used to treat an infection, an infestation, a neoplasm, or an autoimmune disease. The novel compounds may also be used to modulate aspects of the immune system, including modulation of Type 1 and Type 2 activity.

4 Claims, 4 Drawing Sheets

OTHER PUBLICATIONS

Andreone et al., In vitro effect of thymosin-alpha1 and interferon-alpha on Th1 and Th2 cytokine synthesis in patients with chronic hepatitis C, *J. Viral Hepatitis* 8:194-201 (2001).
Azar et al., "Type I (Insulin-dependent) diabetes is a Th1- and Th2-mediated autoimmune disease" *Clin. Diagnos. Lab. Immunol.* 6:306-310 (1999).
Barnard, D., "Viramidine Ribapharm" *Curr. Opin. Inv. Drugs* 3:1585-1589 ((2002).
Begemann et al., "Enhancing the response to interferon-alpha" *J. Clin. Virol.* 13:1-7 (1999).
Berry et al., "Synthesis and Biological Activity of the Novel Adenosine Analogs," *Nucleosides Nucleotides*, 13(1-3), 405-420 (1994).
Bonnet et al., "Modulation of leukocyte genetic expression by novel purine nucleoside analogues. A new approach to antitumor and antiviral agents" *J. Med. Chem.* 36:635-653 (1993).
Bradley et al., "Islet-specific Th1, but not Th2, cells secrete multiple chemokines and promote rapid induction of autoimmune diabetes" *J. Immunol.* 162:2511-2520 (1999).
Brillanti et al., "A pilot study of combination therapy with ribavirin plus interferon alfa for interferon alfa-resistant chronic hepatitis C" *Gastroenterology* 107:812-817 (1994).
Chen, "Guanosine derivatives as immunosimmulants, discovery of loxoribine" *Nucleosides Nucleotides* 13(1-3):551-562 (1994).
DeClercq et al., "Antirhinovirus activity of purine nucleoside analogs," *Antimicrobial Agents and Chemotherapy*, 29:482-487 (1986).
Edwards et al., "The effect of an intralesional sustained-release formulation of interferon alfa-2b on basal cell carcinomas" *Arch. Dermatol.* 126(8)1029-1032 (1990).
Eppstein et al., "Liposomal interferon-beta: sustained release treatment of simian varicella virus infection in monkeys" *J. Infect. Dis.* 159(4):616-620 (1989).
Fan et al., "Circulating Th1 and Th2 cytokines in patients with hepatitis c virus infection" *Mediators of Inflammation* 7:295-297 (1998).
Fraschini et al., "Ribavirin influence on theophylline plasma levels in adult and children" *Int. J. Clin. Pharmacol. Ther. Toxicol.* 26:30-32 (1988).
Gabrielsen et al., "Synthesis and antiviral evaluation of N-carboxamidine-substituted analogues of 1-beta-D-ribofuranosyl-1,2-4-triazole-3-carboxamidine hydrochloride" *J. Med. Chem.*, 35:3231-3238 (1992).
Gallichan et al., "Pancreatic IL-4 expression results in islet-reactive Th2 cells that inhibit diabetogenic lymphocytes in the nonobese diabetic mouse" *J. Immunol.* 163:1696-1703 (1999).
Gerlach et al., "Recurrence of hepatitis C virus after loss of virus-specific CD4(+) T-cell response in acute hepatitis C" *Gastroenterol.* 117:933-941 (1999).
Girardet et al. "Synthesis and citotoxicity of 4-amino-5oxopyridol{2,3-d] pyrimidine nucleosides" *J. Med. Chem.* 43:3704-3713 (2000).
Golumbek et al., "Controlled release, biodegradable cytokine depots: a new approach in cancer vaccine design" *Cancer Res.* 53:5841-5844 (1993).
Hanna et al., "Synthesis of Certain 5'-Substituted Derivatives of Ribavirin and Tiazofurin," *Nucleosides Nucleotides*, 5(4), 343-362 (1986).
Hassig et al., "The role of the Th-1 to Th-2 shift of the cytokine profiles of CD4 helper cells in the pathogenesis of autoimmune and hypercatabolic diseases" *Med. Hypotheses* 51:59-63 (1998).
Hinshaw et al., "A study on the relative chemical reactivity of the 5-cyano group of the nucleoside antibiotic toyocamycin and desaminotoyocamycin. The synthesis of analogs of sangivamycin" *J. Org. Chem.* 35:236-241 (1970).
Hohlfeld, "Biotechnological agents for the immunotherapy of multiple sclerosis" *Brain* 120:865-916 (1997).
Jiang et al., "In vitro and in vivo growth inhibition of SC-M1 gastric cancer cells by retinoic acid" *Oncology* 53(4):334-340 (1996).
Kim et al., Chem Abstract 116:3391 (1991).
Kini et al., "Synthesis and antitumor activity of ribavirin imidates. A new facile synthesis of ribavirin amidine (1-beta-D-ribofuranosyl-1,24-triazole-3-carboxamidine hydrochloride" *J. Med. Chem.* 32(7):1447-1449 (1989).
Kini et al. "Synthesis and antiviral activity of certain guanosine analogues in the thiazolo[4,5-d]pyrimidine ring system" *J. Med Chem.* 34:3006-3010 (1991).
Lollini et al., "Systemic effects of cytokines released by gene-transduced tumor cells: marked hyperplasia induced in small bowel by gamma-interferon transfectants through host lymphocytes" *Int. J. Cancer* 61:425-430 (1995).
Marumo et al., "Application of the interferon minipellet to human renal cell carcinoma in nude mice" *Int. J. Urol.* 4:55-61 (1997).
Neuhaus et al., "Multiple sclerosis: Comparison copolymer-1-reactive t cell lines from treated and untreated subjects reveals cytokine shift from T helper 1 to T helper 2 cells" *Proc. Natl. Acad. Sci. USA* 97:7452-7457 (2000).
Ning et al., "Ribavirin inhibits viral-induced macrophage production of TNF, 1L-1, the procoagulant fgl2 prothrombinase and preserves Th1 cytokine production but inhibits Th2 cytokine response" *J. Immunol.* 160:3487-3493 (1998).
Palmer et al., "Persistent augmentation of natural-killer- and T-cell-mediated cytotoxicity in peripheral blood mononuclear cells pulsed in vitro with high-dose recombinant interleukin-2 prior to culturing with a low maintenance dose" *Cancer Immunol. Immunother.* 39:34-40 (1994).
Pharmaprojects. PJB Publications Ltd., Apr. 2003.
Pifat et al., "Toxicity Evaluation 1-beta-D-ribofuranosyl-1,2,4-triazole-3 carboxamidine hydrochloride (AVS 206) in rhesus monkeys: Comparison with ribavirin" *Antiviral Res.* 9:136 (1988).
Ramasamy et al., "Nucleoside Peptides. 8. Synthesis of Certain Peptide Derivatives of Ribavirin and Tiazofurin," *Nucleosides Nucleotides*, 6(5), 901-911 (1987).
Riskalla, et al. "Synthesis of some 8(beta-D-ribofuranosyl)pyrido[2,3-d]pryimidines structurally related to the antibiotic sangivamycin" *J. Org. Chem.* 57:3980-3985 (1978).
Robinson et al., "Inhibition of hormone-dependent and independent breast cancer cell growth in vivo and in vitro with the antiestrogen toremifene and recombinant human interferon-alpha 2" *Breast Cancer Res. Treat.* 15:95-101 (1990).
Ruther, et al., "Herpes-Simplex-Assozierte Exaserbation Eines Morbus Crohn," *Dtsch. Med. Wschr.* 117:46-50 (1992).
Sanghvi et al., "Growth inhibition and induction of cellular differentiation of human myeloid leukemia cells in culture by carbamoyl congeners of ribavirin," *J. of Med Chem.* 33:336-344 (1990).
Sidwell, "Broad-spectrum antiviral activity of Virazole: 1-beta-D-ribofuranosyl-1,2,4-triazole-3-carboxamidine" *Science* 177:705-706 (1972).
Sidwell, "Effects of ribamidine, a 3-carboxamidine derivative of ribavirin, on experimentally induced *Phlebovirus* infections" *Antiviral Res.* 10:193-208 (1988).
Smee, "Broad-spectrum in vivo antiviral activity of 7-thia-8-oxoguanosine, a novel immunopotentiating agent" *Antimicrob. Agents Chemotherapy* 33:1487-1492 (1989).
Smee, "Antiviral activity of the novel immune modulator 7-thia-8-oxoguanosine" *J. Biol. Response Mod.* 9::24-32 (1990).
Smee, "Immunoenhancing properties and antiviral activity of 7-deazaguanosine in mice" *Antimicrob. Agents Chemotherapy* 35:152-157 (1991).
Smee et al., "Treatment of lethal Pichinde virus infections in weaning LVG/Lak hamsters with ribavirin, ribamidine, selenazofurin, and ampligen" *Antiviral Res.* 20:57-70 (1993).
Srivastava et al., "Synthesis and Antiviral Activity of Certain Thiazole C-nucleosides," *J. of Med Chem.*, 20(2), 256-262 (Feb. 1977).
Srivastava et al., "Synthesis and Antitumor Activity of 2-.beta.-D-Ribofuranosylselenazole-4-carboxamide and Related Compounds," *J. of Med Chem.*, 26(3), 445-448 (Mar. 1983).
Tam et al. "Contact hypersensitivity responses following ribavirin treatment in vivo are influced by Type I cytokine polarization, regulation of IL-10 expression, and costimulatory signaling," *J. Immunol* 163:3709-3717 (1990).

Wang et al., "Synthesis and cytokine modulation properties of Pyrrolo[2,3-d]-4-pyrimidone nucleosides," *J. Med. Chem.* 43:2566-2574 (2000).

Watson, J., "Prospects for hepatitis C virus therapeutics: Levovirin and viramidine as improved derivatives of ribavirin" *Curr. Opin. Inv. Drugs* 3:680-683 (2002).

Witkowski et al., "Design, synthesis, and broad spectrum antiviral activity of 1-beta-D-ribofuranosyl-1,2,4-triazole-3-carboxamide and related nucleosides" *J. Med. Chem.* 15(11): 1151-1152 (1972).

Witkowski et al., "Synthesis and Antiviral Activity of 1,2,4-triazole-3-thiocarboxamidine and 1,2,4-triazole-3-carboxamidine ribonucleosides" *J. Med. Chem.* 16:935-937 (1973).

Wu et al., "Activation and deactivation of a broad-spectrum antiviral drug by a single enzyme: adenosine deaminase catalyzes two consecutive deamination reactions" *Antimicrob. Agents Chemotherapy* 47:426-431 (2003).

Fried et al., "Therapy of chronic hepatitis B with a 6-month course of ribavirin" *J. Hepatol.* 21:145-150 (1994).

Reichard et al., "Randomised, double-blind, placebo-controlled trial of interferon alpha-2b with and without ribavirin for chronic hepatitis C" *Lancet* 351:83-87 (1998).

* cited by examiner

NUCLEOSIDE ANALOGS WITH CARBOXAMIDINE MODIFIED MONOCYCLIC BASE

CROSS-REFERENCE TO RELATED APPLICATIONS

This application is a continuation-in-part of U.S. application Ser. No. 09/595,365, filed Oct. 5, 2000, now U.S. Pat. No. 6,455,508, which claims priority of U.S. provisional application No. 60/182,676 filed Feb. 15, 2000.

FIELD OF THE INVENTION

The present invention relates to the field of nucleoside analogs.

BACKGROUND OF THE INVENTION

Ribavirin (1-β-D-ribofuranosyl-1,2,4-triazole-3-carboxamide) is a nucleoside analog that has demonstrated efficacy in treating viral diseases both as monotherapy (respiratory syncytial virus, Hall, C. B.; McBride, J. T.; Walsh, E. E.; Bell, D. M.; Gala, C. L.; Hildreth, S.; Ten Eyck, L. G.; W. J. Hall. Aerosolized ribavirin treatment of infants with respiratory syncytial viral infection. *N. Engl. J. Med.* 1983, 308, 1443-1447), and in combination therapy with interferon-alpha (hepatitis C virus, Reichard, O.; Norkrans, G.; Fryden, A.; Braconier, J-H.; Sonnerborg, A.; Weiland, O. Randomized, double blind, placebo controlled trial of interferon alpha 2B with and without ribavirin for chronic hepatitis C. *Lancet* 1998, 351, 83-87). Recently reported studies indicate that the in vivo utility of ribavirin can result not only from direct inhibition of viral replication, but also from its ability to enhance T cell-mediated immunity (Hultgren, C.; Milich, D. R.; Weiland, O.; Sallberg, M. The antiviral compound ribavirin modulates the T helper Type1/Type2 subset balance in hepatitis B and C virus-specific immune responses. *J. Gen. Virol.* 1998, 79, 2381-2391; Ning, Q.; Brown, D.; Parodo, J.; Cattral, M.; Fung, L.; Gorczynski, R.; Cole, A.; Fung, L.; Ding, J. W.; Liu, M. F.; Rotstein, O.; Phillips, M. J.; Levy, G. Ribavirin inhibits viral-induced macrophage production of tumor necrosis factor, interleukin-1, procoagulant activity fgl2 prothrombinase and preserves Th1 cytokine production but inhibits Th2 cytokine response. *J. Immunol.* 1998, 160, 3487-3493; Martin, M. J.; Navas, S.; Quiroga, J. A.; Pardo, M.; Carreno, V. Effects of the ribavirin-interferon alpha combination on cultured peripheral blood mononuclear cells from chronic hepatitis C patients. *Cytokine* 1998, 79, 2381-2391. This immunomodulatory effect of ribavirin is demonstrable in vitro by measuring the levels of Type 1 cytokines produced by activated T cells from both humans and mice (Tam, R. C.; Pai, B.; Bard, J.; Lim, C.; Averett, D. R.; Phan, U. T.; Milovanovic, T. Ribavirin polarizes human T cell responses towards a Type 1 cytokine profile. *J. Hepatol.* 1999, 30, 376-382), and by other measures. The induction of a Type 1 cytokine bias by ribavirin is functionally significant in vivo in murine systems (Tam, R. C.; Lim, C.; Bard, J.; Pai, B. Contact hypersensitivity responses following ribavirin treatment in vivo are influenced by Type 1 cytokine polarization, regulation of IL-10 expression and costimulatory signaling. *J. Immunol.* 1999, 163, 3709-3717).

Mammalian immune systems contain two major classes of lymphocytes: B lymphocytes (B cells), which originate in the bone marrow; and T lymphocytes (T cells) that originate in the thymus. B cells are largely responsible for humoral immunity (i.e., antibody production), while T cells are largely responsible for cell-mediated immunity.

T cells are generally considered to fall into two subclasses, helper T cells and cytotoxic T cells. Helper T cells activate other lymphocytes, including B cells and cytotoxic T cells, and macrophages, by releasing soluble protein mediators called cytokines that are involved in cell-mediated immunity. As used herein, lymphokines are a subset of cytokines.

Helper T cells are also generally considered to fall into two subclasses, Type 1 and Type 2. Type 1 cells produce interleukin 2 (IL-2), tumor necrosis factor (TNFα) and interferon gamma (IFNγ), and are responsible primarily for cell-mediated immunity such as delayed type hypersensitivity and antiviral immunity. In contrast, Type 2 cells produce interleukins, IL-4, IL-5, IL-6, IL-9, IL-10 and IL-13, and are primarily involved in assisting humoral immune responses such as those seen in response to allergens, e.g. IgE and IgG4 antibody isotype switching (Mosmann, 1989, *Annu Rev Immunol,* 7:145-173).

As used herein, the terms Type 1 and Type 2 "responses" are meant to include the entire range of effects resulting from induction of Type 1 and Type 2 lymphocytes, respectively. Among other things, such responses include variation in production of the corresponding cytokines through transcription, translation, secretion and possibly other mechanisms, increased proliferation of the corresponding lymphocytes, and other effects associated with increased production of cytokines, including motility effects.

Previous applications (Ser. Nos. 09/462,714, 09/291,097, 09/291,093, 09/471,513, 60/164,365, 60/164,366, 60/172,097, 60/175,111), each of which is incorporated herein by reference, relate to aspects of our recent discoveries involving the effect of various nucleosides (which are defined herein to include derivatives and analogs of native nucleosides) on selectively modulating lymphocyte responses relative to each other. Among other things, we have shown that either of Type 1 and Type 2 responses can be selectively suppressed while the other is either induced or left relatively unaffected, and either of Type 1 or Type 2 responses can be selectively induced while the other is either suppressed or left relatively unaffected. We have also discovered the surprising fact that some nucleosides effective in selectively modulating Type 1 and Type 2 responses relative to one another tend to have a bimodal effect. Among other things, some nucleosides that tend to generally suppress or induce both Type 1 and Type 2 activity at a relatively higher dose tend to selectively modulate Type 1 and Type 2 relative to each other at relatively lower doses.

Viramidine™ (1-β-D-ribofuranosyl-1,2,4-triazole-3-carboxamidine hydrochloride) has been shown active in ten different viruses that is comparable to Ribavirin. (J. T. Witkowski, R. K. Robins, G. P. Khare, R. W. Sidwell, *J. Med. Chem.,* 16, 935-937, 1973; R. W. Sidwell, J. H. Huffman, D. L. Barnard, D. Y. Pifat, *Antiviral Research,* 10, 193-208, 1988; B. Gabrielsen, M. J. Phelan, L. Barthel-Rosa, C. See, J. W. Huggins, D. F. Kefauver, T. P. Monath, M. A. Ussery, G. N. Chmurny, E. M. Schubert, K. Upadhya, C. Kwong, D. A. Carter, J. A. Secrist III, J. J. Kirsi, W. M. Shannon, R. W. Sidwell, G. D. Kini, R. K. Robins, *J. Med. Chem.,* 35, 3231-3238, 1992). In addition, Viramidine™ like Ribavirin is an inhibitor of IMP dehydrogenease (R. C. Willis, R. K. Robins, J. E. Seegmiller, *Molecular Pharmacology,* 18, 287-295, 1980). Furthermore, preliminary toxicology studies suggests that Viramidine™ is less toxic than ribavirin (D. Y. Pifat, R. W. Sidwell, P. G. Canonico, *Antiviral Research,* 9, 136, 1988). Also, recent studies at our lab (R. Tam, K. Ramasamy, ICN Pharmaceuticcals, Inc., unpublished results, 1999)

revealed that Viramidine™ and ribavirin exhibited similar immunomodulatory properties. These results coupled with low bioavailability and the toxicity associated with ribavirin prompt us not only to develop Viramidine™ for other viral diseases but also to prepare other derivatives of Virainidine™, including the synthesis of prodrugs of Viramidine™, and screen them as potential antiviral agents.

The effect of other nucleoside analog compounds on selectively modulating lymphocyte responses relative to each other has not been previously studied or documented. We have discovered that the bimodal effect, or selective modulation of Type 1 and Type 2 responses relative to one another, also occurs after administration of other nucleoside analog compounds, such as pro-drug forms of the compounds.

There are many barriers to overcome in developing biologically active compounds into clinically useful agents. Many potent biologically active compounds never become clinically useful agents because of their undesirable biopharmaceutical properties which include low bioavailability due to low permeability through biological barriers, such as the blood brain barrier (BBB) and the intestinal barrier. Although many factors affect the bioavailability of a drug, the undesirable physicochemical properties (e.g., charge, lipophilicity, hydrogen bonding potential, size) of many drugs is probably one of the most commonly encountered factors that hinder the permeation of drugs through biological barriers. Therefore, optimization of the physicochemical characteristics (charge, lipophilicity, hydrogen bonding potential, size) of a drug is probably the most likely general strategy to facilitate the transport of drugs through such membrane barriers.

To optimize the physicochemical properties of drugs, one possible strategy is that of prodrugs. (H. Bulidgaard, *Design of Prodrugs*, Elsevier, Amsterdam, 1985; N. Bodor, L. Prolkai, W. M. Wu, H. Farag, S. Jonalagadda, M. Kawamura, J. Simpkins, *Science,* 257, 1698-1700, 1992; H. E. Taylor, K. B. Sloan, *J. Pharm. Sci,* 87, 5-20, 1998). The term prodrug is used to describe an agent, which must undergo chemical or enzymatic transformation to the active or parent drug after administration, so that the metabolic product or parent drug can subsequently exhibit the desired pharmacological response. By derivatizing certain polar functional groups in small organic molecules transiently and bioreversibly, the undesirable physicochemical characteristics (e.g., charge, hydrogen bonding potential) of these groups have been "masked" without permanently altering the pharmacological properties of the molecules. This strategy has been very successfully used in cases where the prodrug derivatization involves converting a carboxyl or a hydroxyl functional group into an ester, which can be readily hydrolyzed in vivo either chemically, or enzymatically. The promising prodrug concept, we anticipate that the introduction of other moieties in the parent drug would increase the bioavailabilty, adsorption and antiviral effects.

Despite the existence of as-yet undefined mechanisms, we have discovered that enormous potential benefits can be derived from selective modulation of Type 1 and Type 2 responses relative to each other. We have concluded, for example, that specific modulation of Type 1 relative to Type 2 can be useful in treating a wide variety of conditions and diseases, ranging from infections, infestations, tumors and hypersensitivities to autoimmune diseases.

These discoveries are especially significant because modern treatment strategies for many of the above-listed diseases have limited effectiveness, significant side effects, or both. Treatment of autoimmune disease, for example, is frequently limited to palliative measures, removal of toxic antibodies (as in myasthenia gravis), and administration of hazardous drugs including corticosteroids, chloroquine derivatives, and antimetabolic or antitumor drugs, and drugs such as cyclosporines that target immune system cells.

SUMMARY OF THE INVENTION

The present invention is directed to novel nucleoside analog compounds and related compounds, such as prodrugs, their therapeutic uses and synthesis.

In one aspect of the invention, there are provided nucleoside analog compounds of Formula 1:

Formula 1

Viramidine™ (ICN 3142)

In yet another aspect of the invention, a pharmaceutical composition comprises a therapeutically effective amount of a Formula 1 carboxamidine, or a pharmaceutically acceptable ester or salt thereof admixed with at least one pharmaceutically acceptable carrier.

In yet another aspect of the invention, a pharmaceutical composition comprises a pro-drug form of a Formula 1 carboxamidine, or a pharmaceutically acceptable ester or salt thereof admixed with at least one pharmaceutically acceptable carrier.

In a further aspect of the invention, a compound according to Formula 1 is used in the treatment of any condition which responds positively to administration of the compound, and according to any formulation and protocol which achieves the positive response. Among other things, it is contemplated that compounds of Formula 1 may be used to treat an infection, an infestation, a cancer, tumor or other neoplasm, giant cell arteritis, or an autoilmlmune disease.

DETAILED DESCRIPTION

Where the following terms are used in this specification, they are used as defined below.

The terms "nucleoside" and "nucleoside analog compound" are interchangeable and refer to a compound composed of any pentose or modified pentose moiety attached to a specific position of a heterocycle, aromatic heterocycle or to the natural position of a purine (9-position) or pyrimidine (1-position) or to the equivalent position in an analog.

The term n "nucleotide" refers to a phosphate ester substituted on the 5'-position of a nucleoside.

The term "heterocycle" refers to a monovalent saturated or unsaturated carbocyclic radical having at least one hetero atom, such as N, O or S, within the ring each available position of which can be optionally substituted, independently, with, e.g., hydroxy, oxo, amino, imino, lower alkyl, bromo, chloro and/or cyano. Included within this class of substituents are purines, pyrimidines.

The term "purine" refers to nitrogenous bicyclic heterocycles.

The term "pyrimidine" refers to nitrogenous monocyclic heterocycles.

The term "D-nucleosides" refers to the nucleoside compounds that have a D-ribose sugar moiety (e.g., Adenosine).

The term "L-nucleosides" refers to the nucleoside compounds that have an L-ribose sugar moiety.

The terms "L-configuration" and "D-configuration" are used throughout the present invention to describe the chemical configuration of the ribofuranosyl moiety of the compounds that is linked to the pyrrolo-pyrimidone portion of the molecule.

The term "C-nucleosides" is used throughout the specification to describe the linkage type that formed between the ribose sugar moiety and the heterocyclic base. In C-nucleosides, the linkage originates from the C-1 position of the ribose sugar moiety and joins the carbon of the heterocyclic base. The linkage that forms in C-nucleosides is carbon-to-carbon type.

The term "N-nucleosides" is used throughout the specification to describe the linkage type that formed between the ribose sugar moiety and the heterocyclic base. In N-nucleosides, the linkage originates from the C—I position of the ribose sugar moiety and joins the nitrogen of the heterocyclic base. The linkage that forms in N-nucleosides is carbon to nitrogen type.

The term "protecting group" refers to a chemical group that is added to, oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term "lower alkyl" refers to methyl, ethyl, n-propyl, isopropyl, n-butyl, t-butyl, i-butyl or n-hexyl. This term is further exemplified to a cyclic, branched or straight chain from one to six carbon atoms.

The term "aryl" refers to a monovalent unsaturated aromatic carbocyclic radical having a single ring (e.g., phenyl) or two condensed rings (e.g., naphthyl), which can optionally be substituted with hydroxyl, lower alky, chloro, and/or cyano.

The term "heterocycle" refers to a monovalent saturated or unsaturated carbocyclic radical having at least one hetero atom, such as N, O, S, Se or P, within the ring, each available position of which can be optionally substituted or unsubstituted, independently, with hydroxy, oxo, amino, imino, lower alkyl, bromo, chloro, and/or cyano.

The term "monocyclic" refers to a monovalent saturated carbocyclic radical having at least one hetero atom, such as O, N, S, Se or P, within the ring, each available position of which can be optionally substituted, independently, with a sugar moiety or any other groups like bromo, chloro and/or cyano, so that the monocyclic ring system eventually aromatized [e.g., Thymidine].

The terms "immunomodulator" and "modulator" are herein used interchangeably and refers to natural or synthetic products capable of modifying the normal or aberrant immune system through stimulation or suppression.

The term "effective amount" refers to the amount of a compound of formula (1) that will restore immune function to normal levels, or increase immune function above normal levels in order to eliminate infection.

The compounds of Formula 1 may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formula 1.

The term "α" and "β" indicate the specific stereochemical configuration of a substituent at an asymmetric carbon atom in a chemical structure as drawn.

The term "enantiomers" refers to a pair of stereoisomers that are non-superimposable mirror images of each other. A mixture of a pair of enantiomers, in a 1:1 ratio, is a "racemic" mixture.

The term "isomers" refers to different compounds that have the same formula. "Stereoisomers" are isomers that differ only in the way the atoms are arranged in space.

"Pharmaceutically acceptable salts" may be any salts derived from inorganic and organic acids or bases.

Compounds

The nucleoside analog compounds of the present invention are generally described by Formula 1:

Formula 1

Figure 1:
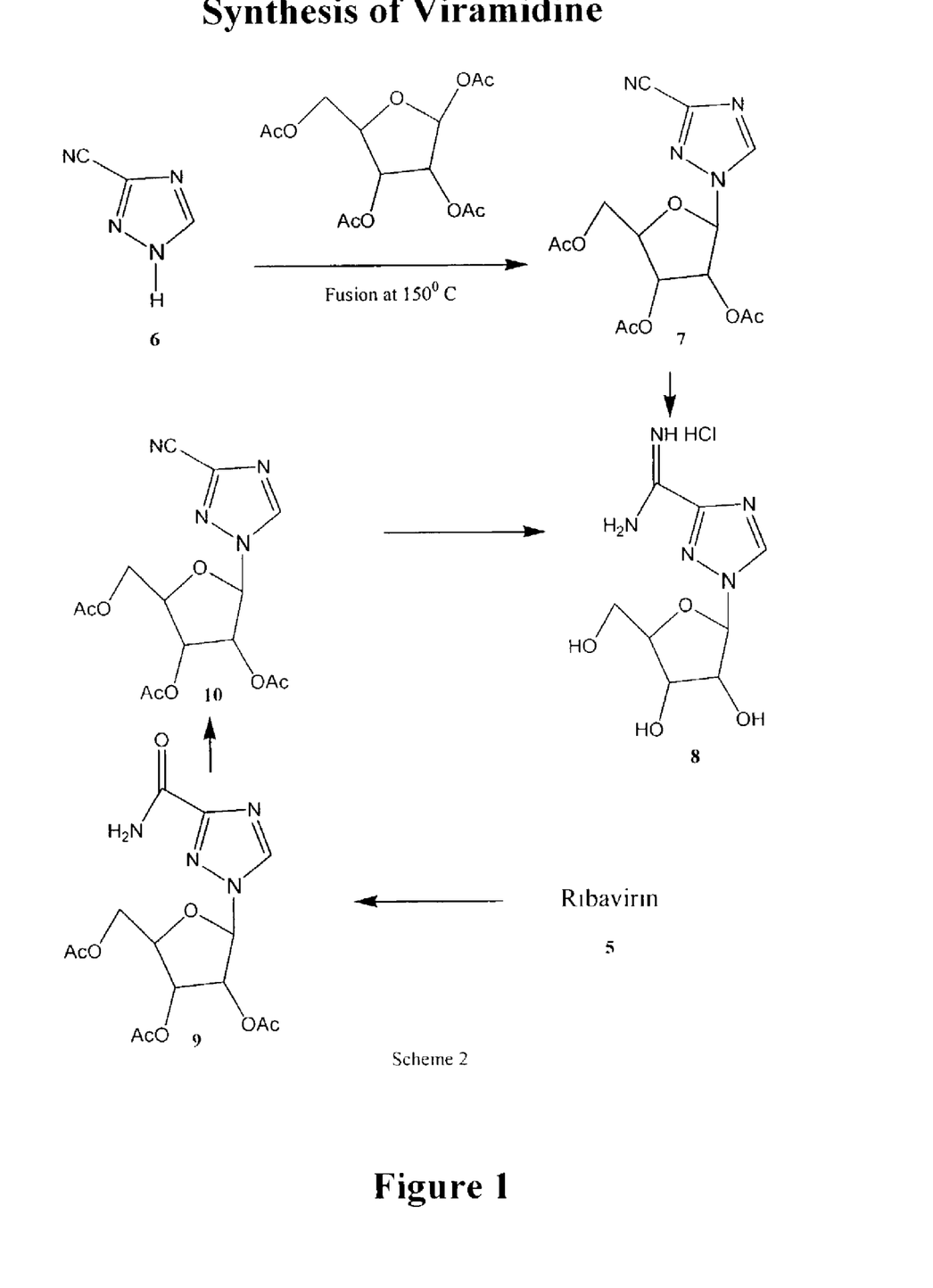
FIG. 1 is an exemplary synthetic scheme for the synthesis of a compound according to Formula 1.

Viramidine™ (ICN 3142)

wherein the chemical configuration of the compound is in the L-configuration or the D-configuration. An exemplary synthesis of contemplated compounds (here: Viramidine™) may follow a procedure as outlined below and shown in FIG. 1.

3-Cyano-1-(2,3,5-tri-O-acetyl-β-D-ribofuranosyl)-1,2,4-triazole (7): A mixture of 3-cyano-1,2,4-triazole (18.8 g, 200 mmol) (6), 1,2,3,5-tetra-O-acetyl-β-D-riboftiranose (63.66 g, 200 mmol) and bis(p-nitrophenyl)phosphate (1 g) were placed in a PB flask (500 mL). The flask was placed in a pre-heated oil bath at 165-175° C. under water aspirator vacuum with stirring for 25 minutes. The acetic acid displaced was collected in a ice cold trap that is placed between aspirator and the RB flask. The flask was removed from the oil bath and allowed to cool. When the temperature of the flask reached roughly to 60-70° C., EtOAc (300 mL) and sat. NaHCO$_3$ (150 mL) were introduced, and extracted in EtOAc. The aqueous layer was extracted again with EtOAc (200 mL). The combined EtOAc extract was washed with sat. NaHCO$_3$ (300 ml), water (200 mL) and brine (150 mL). The organic extract was dried over anhydrous Na$_2$SO$_4$, filtered and the filtrate evaporated to dryness. The residue was dissolved in ether (100 mL) which on cooling at 0° C. for 12 h provided colorless crystals. The solid was filtered, washed with minimum cold EtOH (20 mL) and dried at high vacuum over solid NaOH. Yield: 56.4 g (80%). mp 96-97° C. $^1$HMR (CDCl$_3$): δ 2.11 (s, 3H, COCH$_3$), 2.13 (s, 3H, COCH$_3$), 2.14 (s, 3H, COCH$_3$), 4.22 (dd, 1H), 4.46 (m, 2H), 5.52 (t, 1H, J=6.0 Hz), 5.70 (m, 1H), 6.01 (d, 1H, C$_1$H J=3.6 Hz) and 8.39 (s, 1H, C$_5$H). Anal. Calc. For C$_{14}$H$_{16}$N$_4$O$_7$ (352.30): C, 47.73; H. 4.58; N, 15.90. Found: C, 47.70; H, 4.63; N, 16.01.

1-β-D-Ribofuranosyl-1,2,4-triazole-3-carboxamidine (Viramidine™) Hydrochloride (8): A mixture of (7) (14.08 g, 40.0 mmol), NH$_4$Cl (2.14 g, 40.0 mmol) and anhydrous ammonia (150 ml) was heated in a steel bomb at 85° C. for 18 h. The steel bomb was cooled, opened and the contents were evaporated to dryness. The residue was crystallized from MeCN-EtOH to provide 10.6 g (95%) of 8. Mp 177-179° C. $^1$HMR (DMSO-d$_6$): δ 3.44-4.2 (m, 3H), 4.40 (m, 2H), 5.04 (t, 1H), 5.29 (m, 1H), 5.74 (in, 1H), 5.87 (d, 1H, C$_1$H), 8.96 (bs, 3H) and 9.17 (s, 1H, C$_5$H). Anal. Calc. For C$_8$H$_{14}$ClN$_5$O$_4$ (279.68): C, 34.35; H, 5.05; N, 25.04; Cl, 12.69. Found: C, 34.39; H, 5.10; N, 25.14; Cl, 12.71.

Alternatively, the synthesis may proceed from commercially available Ribavirin™ as follows:

2',3',5'-Tri-O-acetyl-1-β-D-ribofuranosyl-1,2,4-triazole-3-carboxamide (9). A suspension of 1-β-D-ribofuranosyl-1,2,4-triazole-3-carboxamide (Ribavirin™) (28.4 g, 116.4 mmol) (5) in acetic anhydride (200 mL) and pyridine (50 mL) was stirred at room temperature overnight. The resulting clear solution was concentrated in vacuo to yield a clear foam (43.1 g, quantitive). This foam was homogenous on TLC and used directly for the next step without purification. A small amount was purified by flash chromatography to yield an analytical sample; $^1$H NMR (300 MHz), DMSO-d$_6$) δ 2.01, 2.08, 2.09 (3s, 9H, COCH$_3$), 4.10 (m, 1H), 3.52 (m, 2H), 5.58 (t, 1H), 5.66 (in, 1H); 6.33 (d, 1H, J.=3.0 Hz, C$_1$H), 7.73, 7.92, (2 s, 2H, CONH$_2$), 8.86 (s, 1H, C$_5$H triazole). Anal. (C$_{10}$H$_{18}$N$_4$O$_8$) C, H, N.

3-Cyano-2',3',5'-tri-O-acetyl-1-β-D-ribofuranosyl-1,2,4-triazole (10). To a solution of 9 (43.1 g, 116.4 mmol) in chloroform (500 mL) was added triethylamine (244 mL) and the mixture cooled to 0° C. in an ice-salt bath. Phosphorus oxychloride (30.7 ml, 330 mmol) was added dropwise with stirring and the solution allowed to warm to room temperature. After the mixture was stirred at room temperature for 1 h, TLC (hexane/acetone 3:1) indicated complete disappearance of starting material. The brown reaction mixture was concentrated to dryness in vacuo and the residue dissolved in chloroform (500 mL). This organic solution was washed with saturated aqueous sodium bicarbonate (3×200 mL), dried over anhydrous sodium sulfate, and concentrated in vacuo. The residue was chromatographed over silica gel (flash chromatography) with 20% acetone in hexane to yield 33.14 g (81% from ribavirin) of pure 10 as an amorphous solid. This solid was identical in all respects with an authentic sample: mp 101-103° C.; IR (potassium bromide) v 2250 (CN), 1750 (C=O), cm$^{-1}$; $^1$H NMR (300 MHz, CDCl$_3$) δ 2.04, 2.06, 2.07 (3 s, 9H, acetyl methyls), 4.15 (dd, 1H), 4.40 (m, 1H), 5.47 (t, 1H), 5.63 (dd, 1H), 5.95 (d, 1H, J=3.2 Hz, C$_1$H), 8.34 (s, 1H, C$_5$H triazole).

1-β-D-Ribofuranosyl-1,2,4-triazole-3-carboxamidine Hydrochloride (8). To a suspension of 10 (4.0 g, 11.4 mmol) in methanol (100 mL) was added a molar solution of methanolic sodium methoxide (12 mL) and the mixture stirred at room temperature overnight. The solution was acidified to pH 4 with methanol washed Dowex H+ resin, the resin was filtered, and the filtrate was concentrated to dryness in vacuo. The residue was dissolved in a minimum amount of methanol (15 mL) and transferred to a pressure bottle. Ammonium chloride (0.61 g, 11.4 mmol) and a solution of methanol saturated at 0° C. with dry ammonia gas (75 mL) were added, the bottle was sealed, and the solution was stirred at room temperature overnight. The solution was concentrated to dryness in vacuo and the resulting residue crystallized from acetonitrile/ethanol to yield 8 as a crystalline solid (2.95 g, 93%). This sample was identical in all respects with an authentic sample.

In certain pharmaceutical dosage forms, the pro-drug form of the compounds, especially including acylated (acetylated or other) derivatives, pyridine esters and various salt forms of the present compounds are preferred and can be administered in a method of treatment of a condition of a patient. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to a targeted site within the host organism or patient to maximize the intended effect of the compound.

A contemplated example of the formation of a pro-drug form of the compounds disclosed herein is as follows. One of the simplest prodrug of Viramidine™ is the tri-O-acetyl derivative of Viramidine™. The tri-O-acetyl derivative is prepared as depicted in scheme 1:

Scheme 1

5'-Retinoyl derivative of Viramidine™ is another simple prodrug form and been prepared as follows:

Scheme 2

-continued

Other 5'-derivatives of Viramidine™ includes the following shown in Scheme 3:

Scheme 3

R = CH₂—(CH₂)₁₃—CH₃
R = O—CH₂—(CH₂)₁₃—CH₃
R = N—CH₂—(CH₂)₁₃—CH₃
R = [imidazole]
R = [steroid with C₈H₁₇]

Most of these compounds may be obtained as described (C. Sergheraert, C. Pierlot, A. Tartar, Y. Henin, M. Lemaitre, *J. Med Chem.*, 36, 826-830, 1993).

Synthesis of coumarin-based prodrug form of Viramidine™ may be obtained as follows:

Scheme 4

[acetylsalicylic acid structure] →  i. EDC/DMAP/Viramidine
ii. HCl/Ether

-continued

Amino acid esters are considered better prodrug forms because of possible involvement of a stereoselective transporter. Amino acid derivatives of Viramidine™ could be synthesized as shown below:

Scheme 5

Z-Amino Acid  →  i. EDC/DMAP/Viramidine
ii. Pd/C/HCl/Dioxane

[Viramidine amino acid ester structure, labeled "Amnio Acid—O"]

For specific delivery of drugs to the liver and the biliary system the endogenous bile acid transport system is an attractive candidate. Synthesis of bile acid conjugates of Viramidine™ could be accomplished as represented below:

Nucleotide derivatives are another class of prodrugs or prodrug forms. Preparation of protected 5'-monophosphate derivatives are shown below. By protecting the negative charges of phosphates with neutral substituents would form more lipophilic derivatives that are expected to revert back to the corresponding monophosphates once inside the cell.

Scheme 6

Cholic Acid  →  i. EDC/DMAP/Viramidine
ii. HCl/Dioxane

Nucleotide derivatives are another class of prodrugs or prodrug forms. Preparation of protected 5'-monophosphate derivatives are shown below. By protecting the negative charges of phosphates with neutral substituents would form more lipophilic derivatives that are expected to revert back to the corresponding monophosphates once inside the cell.

Scheme 7 i. 1H-Tetrazole/ HF/Viramidine
ii. ClCH$_6$H$_4$CO$_3$H/ CH$_2$Cl$_2$
iii. HCl/Dioxane where R$_1$ is alkyl groups such as CH$_3$C(O)S—CH$_2$CH$_2$—; (CH$_3$)$_2$CHC(O)S—CH$_2$CH$_2$—; (CH$_3$)$_3$CC(O)S—CH$_2$CH$_2$—; (CH$_3$)$_3$CC(O)OCH$_9$—; C$_6$H$_5$C(O)S—CH$_2$CH$_2$— or HOCH$_2$CH$_2$SS—CH$_2$CH$_2$—.

Amino acid phosphoramidates are another class of prodrugs that could be synthesized as described below:

Scheme 8

R = Anything Except Hydrogen

Other derivatives of monophosphate prodrugs are shown below:

Scheme 8A i. R—S—S—Ph—CH$_2$—OH/ N,N'-Carbonyldiimidazole
ii. HCl/Dioxane

R = Alkyl, Lipids, vitamins, bile acids, Cholesterol derivatives

Salicylate-based prodrugs of Viramidine™ may be obtained by the following scheme:

Scheme 9

R$_1$ = CH$_3$
R$_1$ = Ph
R$_1$ = H
R$_1$ =

Prodrugs of nucleoside 5'-di or triphosphates would be more interesting since they would bypass more metabolic steps.

Following are potential nucleotide lipophilic prodrugs and are prepared as depicted below:

Following is another class of potential phosphonate prodrug of Viramidine™:

Scheme 12

Other possible prodrugs include the possible combinations of the groups shown in PCT patent application WO 98/39342, WO 98/39343, WO 98/39344 and WO 99/45016.

Prodrugs of Viramidine™ could be obtained not only by modifying the sugar portion of the parent molecule but also by derivatizing the amidine functionality too. Following are a few classes of prodrugs that may be prepared by modifying the amidine group as described below:

Scheme 13

Scheme 14

Scheme 15

Scheme 16 i. R—CH$_2$—OH/
N, N'-Carbonyldiimidazole
i. HCl/Dioxane

-continued

R = CH₃——
R = Phenyl
R = R₁——S——S——Ph—— and
R₁ = Alkyl, Lipids, vitamins, bile acids, Cholesterol derivatives Uses It is contemplated that compounds according to Formula 1 will be used to treat a wide variety of conditions, and in fact any condition which responds positively to administration of one or more of the compounds. Among other things it is specifically contemplated that compounds of the invention may be used to treat an infection, an infestation, a cancer or tumor or an autoimmune disease. It is further contemplated that the compounds of the invention may be used to target conditions or diseases in specific organs of a patient, such as the liver or heart.

Infections contemplated to be treated with the compounds of the present invention include respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), measles, and fungus.

Infestations contemplated to be treated with the compounds of the present invention include protozoan infestations, as well as helminth and other parasitic infestations.

Cancers or tumors contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Autoimmune and other diseases contemplated to be treated include arthritis, psoriasis, bowel disease, juvenile diabetes, lupus, multiple sclerosis, gout and gouty arthritis, rheumatoid arthritis, rejection of transplantation, giant cell arteritis, allergy and asthma.

Still other contemplated uses of the compounds according to the present invention include use as intermediates in the chemical synthesis of other nucleoside or nucleotide analogs that are, in turn, useful as therapeutic agents or for other purposes.

In yet another aspect, a method of treating a mammal comprises administering a therapeutically and/or prophylactically effective amount of a pharmaceutical containing a compound of the present invention. In this aspect the effect may relate to modulation of some portion of the mammal's immune system, especially modulation of lymphokines profiles of Type 1 and Type 2 with respect to one another. Where modulation of Type 1 and Type 2 lymphokines occurs, it is particularly contemplated that the modulation may include suppression of both Type 1 and Type 2, and more preferably stimulation of Type 1 lymphokines, or a relative increase of a type 1 response to a type 2 response.

Figure 2:
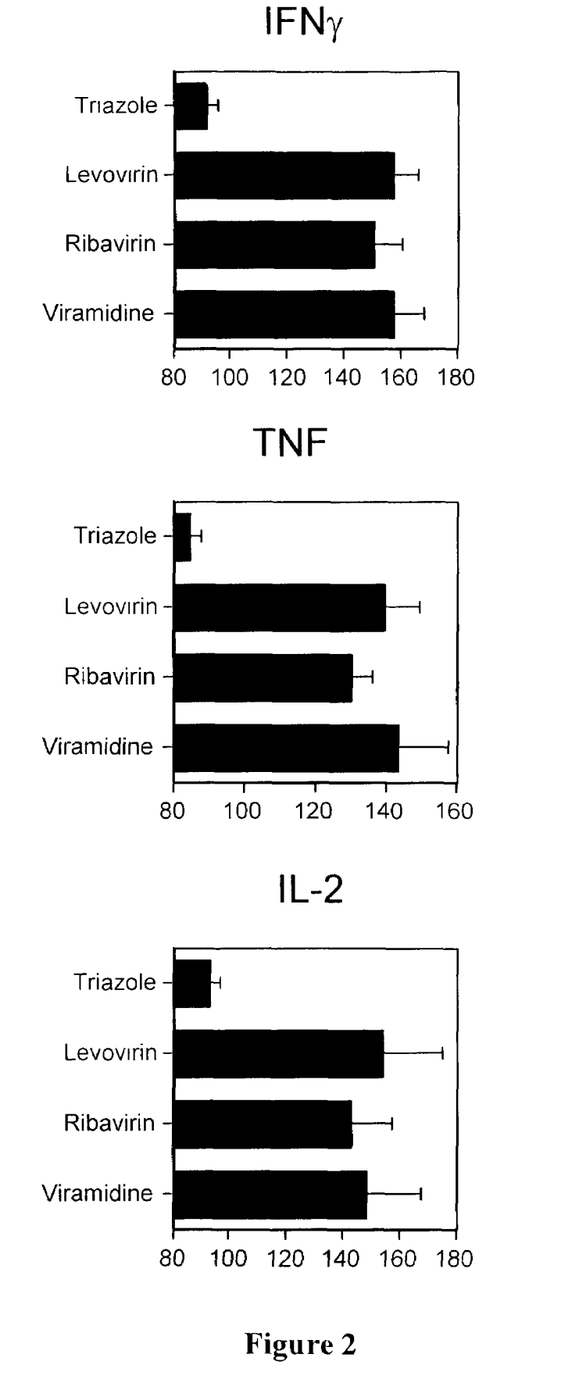
FIG. 2 is a graphical depiction of the effect of contemplated and other compounds on Type 1 cytokine synthesis in SEB-activated human T cells.
Figure 3:
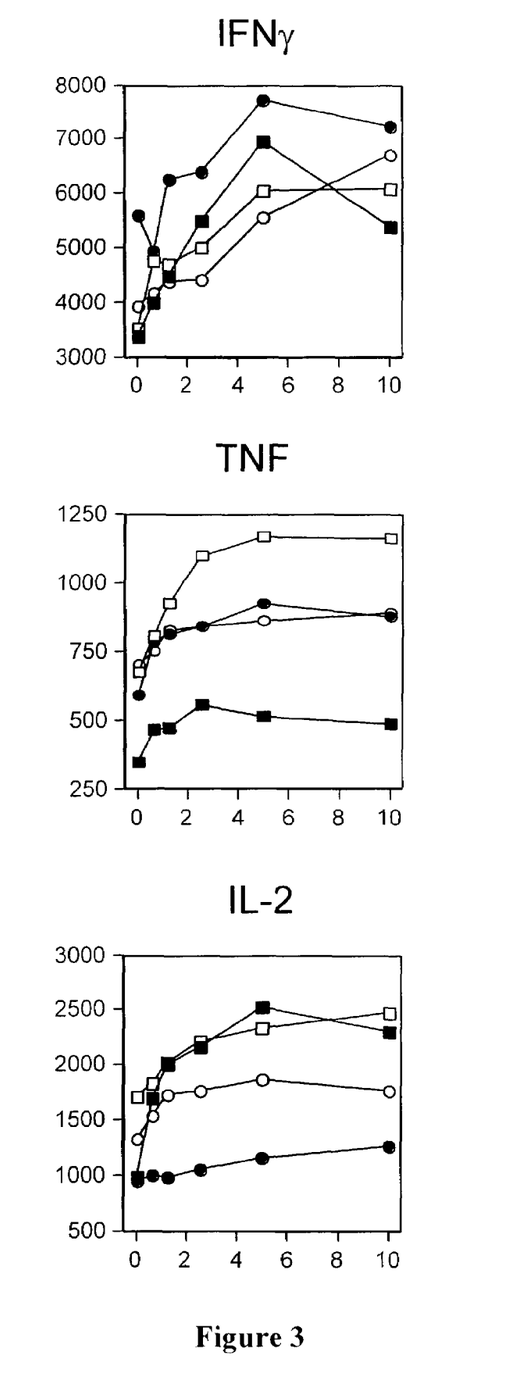
FIG. 3 is a graphical depiction of the effect of 0.625-10 µM concentration of a contemplated compound on Type 1 cytokine synthesis in SEB-activated human T cells.
Figure 4:
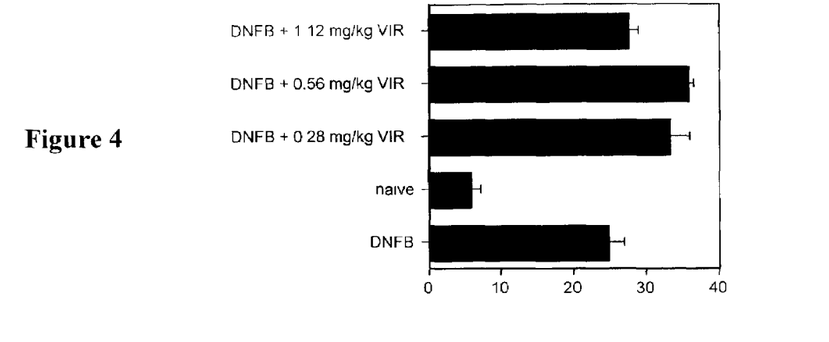
FIG. 4 is a graphical depiction of the Effect of a contemplated compound on CHS responses in BALB/c mice.
Figure 5:
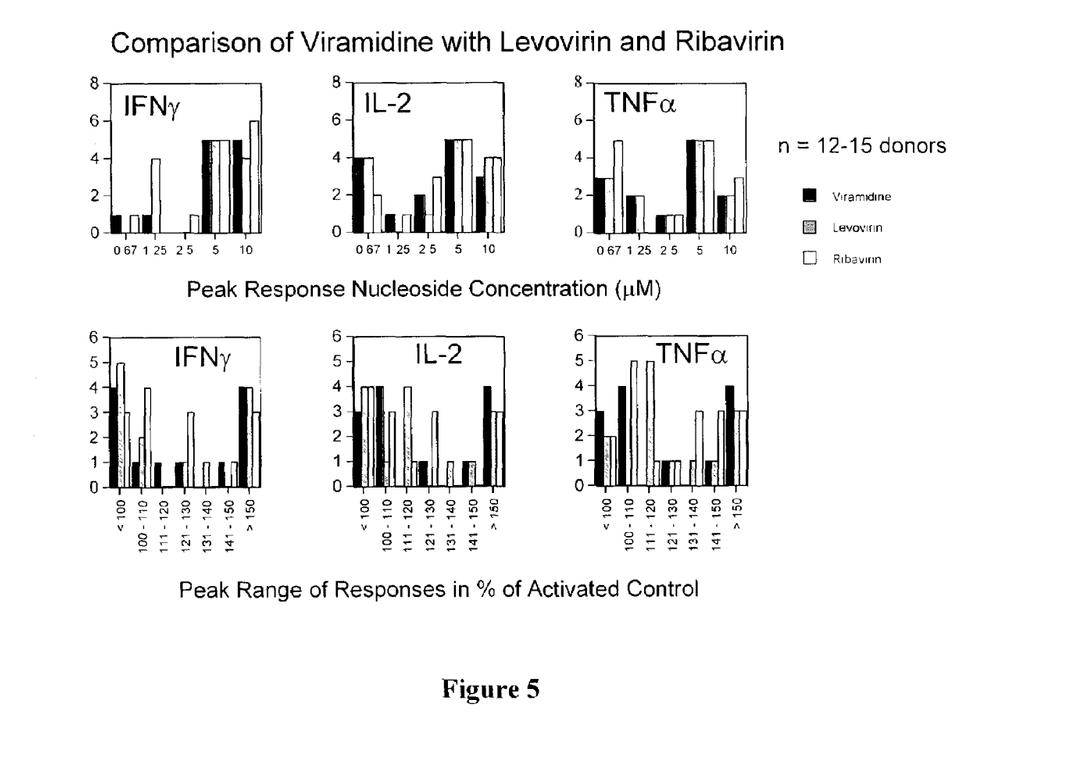
FIG. 5 is a graphical depiction of the peak response and peak range of contemplated and other compounds on Type 1 cytokine synthesis in SEB-activated human T cells.

It is particularly contemplated that Viramidine™ (1.39 μg/ml) increases the expression and synthesis of Type 1 cytokines in (preferably activated) T-lymphocytes, and results from various experiments are shown in FIGS. 2-5. FIG. 2 depicts the effect of 5 μM Viramidine (a compound according to Formula 1), Ribavirin, and levovirin on Type 1 cytokine synthesis in SEB-activated human T cells (n=5 donors), in which viramidine shows a clear increase in the Type 1 response as compared to the control with Triazole. FIG. 3 is a graphical representation of a dose-response effect of Viramidine in the range of 0.625-10 μM on Type 1 cytokine synthesis in SEB (Staphylococcal Enterotoxin B)-activated human T cells (data represent 4 individual donors). The in vivo effect of an increased Type 1 response in a contact hyper-sensitivity (CHS) assay of Viramidine is clearly demonstrated in FIG. 4, and FIG. 5 shows a comparison between Viramidine and Levovirin/Ribavirin in respect to peak response nucleoside concentration and peak range of responses (y-axis depicts number of responders in a particular experiment).

Preparation of Human T-Cells and Activation In Vitro

Peripheral blood mononuclear cells were isolated from healthy donors or rheumatoid arthritis patients by density gradient centrifugation followed by T cell enrichment using Lymphokwik (One Lambda, Canoga Park Calif.). Contaminating monocytes were removed by adherence to plastic. Purified T cells were >99% CD2+, <1% HLA-DR+ and <5% CD25+ and were maintained in RPMI-AP5 (RPMI-1640 medium containing 20 mM HEPES buffer, pH 7.4, 5% autologous plasma, 1% L-glutamine, 1% penicillin/streptomycin and 0.05% 2-mercaptoethanol).

For determination of cytokine protein levels, T-cells ($1 \times 10^6$ cells in a volume of 1 ml) were activated by the addition of 10 ng PMA plus 0.5 μg ionomycin (both from Calbiochem, La Jolla, Calif.) and incubated in 24 well plates in the presence of 0 to 20 μM nucleoside for up to 48 h at 37° C. and 5% $CO_2$ in a humidified incubator. Following activation, supernatants were analysed for cell-derived cytokine production. For proliferation and viability studies, the protocol as above was modified to a 96 well-plate format using $0.2 \times 10^6$ cells in a volume of 0.2 ml and activation with 2 ng PMA and 0.1 μg ionomycin. In separate experiments, $5 \times 10^6$ T cells in 2 ml were activated with 20 ng PMA plus 1 μg ionomycin. Alternatively, cells can be activated in vitro with SEB following published procedures. Here total RNA was isolated from T cells following 6-24 h incubation and analyzed by RT-PCR to determine mRNA levels of various cytokines and inflammatory mediators. Also in separate experiments, human T cells were purified further (using cell enrichment reagents from Stem Cell Technologies, Vancouver, BC) to give pure populations of CD4+ (<1% CD8+ using RosetteSep human CD4+ T cell isolation reagent), and CD8+ (<1% CD4+ using RosetteSep human CD4+ T cell isolation reagent) T cell subsets, after which $1 \times 10^6$ cells per ml were activated with PMA and ionomycin, as in the total T cell experiments.

Extracellular Cytokine Analyses

Human cytokine levels were determined in cell supernatants, following appropriate dilution, using ELISA kits specific for IL-2, IFNg, TNFa, IL-4 and IL-5 (Biosource International, Camarillo, Calif.). Murine cytokine levels were determined using ELISA kits specific for murine IFNg and IL-4 (R and D Systems, Minneapolis, Minn.). All FLISA results were expressed as pg/ml. Some data are shown as percentage of activated control, calculated as the ratio of activated T cell cytokine level in the presence of test nucleoside over the cytokine level of untreated activated T cells×

100%. Zero effect on cytokine levels by test nucleosides would give a percentage of activated control value of 100%. Alternatively data were shown as percentage change from activated control ([(test pg/ml–activated control pg/ml)/activated control pg/ml]×100%). Zero effect on cytokine levels by test nucleosides would be 0%.

Contact Hypersensitivity (CHS)

Reactivity to the contact allergen, DNFB, was determined, in BALB/c mice, as previously described (Ishii, N., K. Takahashi, H. Nakaiima, S. Tanaka, P. W. Askenase. 1994. DNFB contact sensitivity (CS) in BALB/c and C3H/He mice. *J. Invest. Dermatol.* 102:321). Briefly, mice were sensitized by application of 20 µl of 0.3% DNFB in acetone: olive oil, 4:1 onto the shaved abdomens of naive mice. For optimal elicitation of CHS, the mice were challenged on both sides of each ear with 20 µl of 0.12% DNFB, five days after sensitization. Unsensitized mice were also challenged and used as controls in each experiment. After 24 h, ear thickness measurements were taken and response to DNFB was assessed by subtracting post-challenge from pre-challenge values. Where indicated, 7-β-D-ribofuranosyl-4-oxopyrrolo[2,3-d]pyrimidine-5-carboxamidine, at a dose of 6.2 µg in 50 µl PBS (0.3 mg/kg) or 12.4 µg in 100 µl PBS (0.6 mg/kg), was administered by i.p. injection at the time of challenge with DNFB. These doses of 7-β-D-riboftiranosyl-4-oxopyrrolo[2,3-d]pyrimidine-5-carboxamidine gave maximal effect in preliminary optimization studies. Following final ear thickness measurements, mice were sacrificed by cervical dislocation and axillary/lateral axillary lymph nodes were removed. Following isolation of total cellular RNA from isolated lymph node cells, RT-PCR and Southern Blot analyses were performed to monitor for mouse IFNg, IL-2, and IL-10 mRNA levels.

Further Experiments

It is generally contemplated that a shift of an immune response towards a Type 1 response is favorable. Consequently, it is contemplated that compounds according to the inventive subject matter may be particularly useful in treatment of viral diseases (preferably in viral infections in which the type 1 response is reduced or suppressed). To confirm the effectiveness of modulating an immune response, various experiments have been conducted, and the following is an exemplary summary of some of the experiments conducted with contemplated compounds:

In vitro—Viramidine inhibited Punta Toro virus infection of LLC-MK2 (rhesus monkey kidney cells) with EC50 of 8 mg/ml (Adaines strain) and 12 mg/ml (Balliet strain)-CC50 was 320 mg/ml (1.0-1.2 virus rating).

In vivo—Administration s.c., or oral viramidine resulted in 100% survival (10 C57BL/6 mice/gp) of PTV injected s.c. (Adames strain).

For 24 h post infection by PTV in vivo the minimum effective s.c. dose of 32 mg/kg for ribavirin and for viramidine was 96 mg/kg given s.c. b.i.d for 5 days. For 24 h post infection by PTV in vivo the minimum effective p.o. dose of 20 mg/kg for ribavirin and for viramidine was 40 mg/kg given p.o. b.i.d for 5 days.

In general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better pharmacokinetics. This result may attain because L-nucleosides may not be recognized by enzymes, and therefore may have longer half-lives.

It is contemplated that compounds according to the present invention will be administered in vivo, in vitro, or ex vivo in any appropriate pharmaceutical formulation, and under any appropriate protocol. Thus, administration may take place orally, parenterally (including subcutaneous injections, intravenous, intramuscularly, by intrasternal injection or infusion techniques), by inhalation spray, or rectally, topically and so forth, and in dosage unit formulations containing conventional non-toxic pharmaceutically acceptable carriers, adjuvants and vehicles.

By way of example, it is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in patients.

In addition, compounds according to the present invention may be administered alone or in combination with other agents for the treatment of the above infections or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect. Preferably, the combination therapy involves the administration of one compound of the present invention or a physiologically functional derivative thereof and one of the agents mentioned herein below.

Examples of other drugs or active ingredients contemplated to be effective in combination with a modulator according to Formula 1 are anti-viral agents such as interferon, including but not limited to interferon α and γ, Ribavirin, acyclovir, and AZT™; anti-fungal agents such as tolnaftate, Fungizone™, Lotriinin™, Mycelex™, Nystatin and Amphoteracin; anti-parasitics such as Mintezol™, Niclocide™, Vermox™, and Flagyl™, bowel agents such as Immodium™, Lomotil™ and Phazyme™; anti-tumor agents such as interferon α, and γ, Adriainycin™, Cytoxan™, Ilmura™, Methotrexate, Mithracin™, M TaXOI™; dermatologic agents such as Aclovate™, Cyclocort™, Denorex™, Florone™, Oxsoralen™, coal tar and salicylic acid; migraine preparations such as ergotamine compounds; steroids and immunosuppresants not listed above, including cyclosporins, Diprosone™, hydrocortisone; Floron™, Lidex™, Topicort and Valisone; and metabolic agents such as insulin, and other drugs which may not nicely fit into the above categories, including cytokines such as IL2, IL4, IL6, IL8, IL1O and IL12. Especially preferred primary drugs are AZT, 3TC, 8-substituted guanosine analogs, 2,3-dideoxynucleosides, interleukin II, interferons such as IαB-interferons, tucaresol, levamisole, isoprinosine and cyclolignans.

Examples of such further therapeutic agents include agents that are effective for the modulation of immune system or associated conditions such as AZT, 3TC, 8-substituted guanosine analogs, 2',3'-dideoxynucleosides, interleukin II, interferons, such as α-interferon, tucaresol, levamisole, isoprinosine and cyclolignans. Certain compounds according to the present invention may be effective for enhancing the biological activity of certain agents according to the present invention by reducing the metabolism or inactivation of other compounds and as such, are co-administered for this intended effect.

With respect to dosage, one of ordinary skill in the art will recognize that a therapeutically effective amount will vary with the infection or condition to be treated, its severity, the treatment regimen to be employed, the pharmacokinetics of the agent used, as well as the patient (animal or human) treated. It is contemplated that various alternative dosages are also appropriate, including dosages between 0.5 mg/kg and 0.1 mg/kg and less, but also dosages between 0.5 and 1.0 mg/kg and more. It is further contemplated that while treatment success may be achieved with some viral infections at relatively low plasma concentrations of the compounds of Formula 1, other viral infections may require relatively high dosages. It is contemplated, however, that an appropriate regimen will be developed by administering a small amount, and then increasing the amount until the side effects become unduly adverse, or the intended effect is achieved.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

What is claimed is:

1. A method of treating a condition in a patient comprising: administering to said patient a therapeutic amount of the compound according to Formula 1, Formula 1 the Formula 1 carboxamidine, or a pharmaceutically acceptable salt or pro-drug form thereof, wherein the compound is in L-configuration or D-configuration, and wherein the condition is selected from the group consisting of an HIV infection, an HCV infection, an HBV infection, and a Human Papilloma Virus infection.

2. The method of claim 1, wherein the condition is an HCV infection.

3. The method of claim 1, further comprising the administration to said patient of an interferon.

4. The method of claim 3, further comprising the administration to said patient of an interferon.

* * * * *

UNITED STATES PATENT AND TRADEMARK OFFICE
CERTIFICATE OF CORRECTION

PATENT NO. : 7,638,496 B2 Page 1 of 1
APPLICATION NO. : 10/227235
DATED : December 29, 2009
INVENTOR(S) : Tam et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1524 days.

Signed and Sealed this

Twenty-first Day of December, 2010

David J. Kappos
*Director of the United States Patent and Trademark Office*